United States Patent [19]

Park et al.

[11] Patent Number: 5,136,046
[45] Date of Patent: Aug. 4, 1992

[54] PREPARATION OF AMINE ALANES

[75] Inventors: Won S. Park; Everett M. Marlett, both of Baton Rouge, La.

[73] Assignee: Ethyl Corporation, Richmond, Va.

[21] Appl. No.: 589,421

[22] Filed: Sep. 28, 1990

[51] Int. Cl.$^5$ .................. C07D 207/00; C07F 5/06
[52] U.S. Cl. ..................... 548/402; 556/170; 556/171; 556/176
[58] Field of Search ............ 548/402; 556/176, 170, 556/171; 423/644

[56] References Cited

U.S. PATENT DOCUMENTS 3,355,262 11/1967 Beaird et al. ............... 423/644

OTHER PUBLICATIONS

Everett M. Marlett and Won Suh Park, "Dimethylethylamine-Alane and N-Methyl-pyrrolidien-Alane. A Convenient Synthesis of Alane, a Useful Selective Reducing Agent in Organic Synthesis." The Journal of Organic Chemistry, 1990, vol. 55.

Primary Examiner—Mary C. Lee
Assistant Examiner—Joseph K. McKane
Attorney, Agent, or Firm—Terry B. Morris; Richard J. Hammond

[57] ABSTRACT

Tertiary amine alanes are produced by reacting sodium aluminum hydride and magnesium dichloride. A tertiary amine is admixed to extract the tertiary amine alane. Stoichiometric ratios of sodium aluminum hydride to magnesium dichloride can be varied to effect the magnesium compound by-product produced.

18 Claims, No Drawings

PREPARATION OF AMINE ALANES

BACKGROUND

Amine alanes eg. $AlH_3 \cdot NR_3$ and $AlH_3 \cdot 2NR_3$) are complexes of tertiary amines $(NR_3)$ with alane, i.e. aluminum hydride $(AlH_3)$ Amine alanes are used in various reduction processes, in the preparation of aluminum, and in the production of silane. See, for example, Marlett, U.S. Pat. No. 4,474,473, issued Oct. 2, 1984; and Brendel, U.S. Pat. No. 3,552,946, issued Jan. 5, 1971.

The production of amine alanes has been accomplished by several methods (see Nelson, Becker, and Kobetz, U.S. Pat. No. 3,651,064, issued Mar. 21, 1972, and references therein).

Dilts and Ashby, Inorg. Chem 9(4), 855 (1970), in a study of complex metal hydrides in tertiary amine solvents, found that trimethylamine extracted alane from lithium aluminum tetrahydride ($LiAlH_4$, also referred to herein as "lithium aluminum hydride") to produce an amine alane, $AlH_3 \cdot 2N(CH_3)_3$.

Dilts and Ashby, in the same study, were unsuccessful in extracting alane from sodium aluminum tetrahydride (also referred to herein as "sodium aluminum hydride") by any amine.

Another route to amine alane is by the production of lithium aluminum hydride by the reaction of lithium chloride with sodium aluminum hydride, as taught by Robinson (French Patent 1,245,361; 1960), followed by extraction with dimethylethylami or N-methylpyrrolidine, as taught by Park and Marlett, J. Org. Chem., 55, 2968 (1990).

In one process for preparation of sodium aluminum hydride, aluminum and hydrogen react with trisodium aluminum hexahydride, $Na_3AlH_6$, under pressure, as taught by Beaird and Kobetz, U.S. Pat. No. 3,355,262, issued Nov. 28, 1967.

SUMMARY

This invention relates to the production of tertiary amine alanes using sodium aluminum hydride ($NaAlH_4$) and magnesium dichloride ($MgCl_2$). Amine alanes are produced by the reaction of sodium aluminum hydride with magnesium dichloride to form magnesium dialuminum hydride or chloromagnesium aluminum hydride, or both, followed by extraction with a tertiary amine to produce an amine alane and a magnesium compound.

DESCRIPTION OF THE PREFERRED EMBODIMENTS

One embodiment of the present invention is a process for producing an amine alane, which process comprises reacting sodium aluminum hydride ($NaAlH_4$), magnesium dichloride ($MgCl_2$) and a tertiary amine ($R_3N$) such that an amine alane and a magnesium compound are produced.

In the above embodiment sodium aluminum hydride is reacted with magnesium chloride to form an intermediate product comprising magnesium dialuminum hydride, $Mg(AlH_4)_2$, or chloromagnesium aluminum hydride, $ClMgAlH_4$, or a mixture of both, followed by the extraction of alane from these complex metal hydrides in the form of an amine alane. The synthesis of amine alane by this process is believed to proceed according either to one or both of the following reaction schemes:

SCHEME I

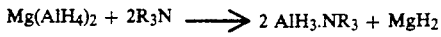

SCHEME II

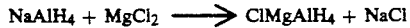

Although both schemes show the reaction of sodium aluminum hydride and magnesium dichloride to form a complex metal hydride, followed by the extraction of an amine alane from the complex metal hydride using a tertiary amine, they demonstrate that the relative stoichiometric quantity of sodium aluminum hydride can control which of the reaction schemes is involved in the process. Unexpectedly, as will be discussed hereinafter, it has been discovered that solvent selection can affect stoichiometric control. Although these two reaction schemes are illustrated as two separate steps, the reaction-extraction sequence can be viewed as a one-step reaction when the tertiary amine is admixed with the sodium aluminum hydride and the magnesium dichloride. This combined reaction - extraction scheme permits the use of a single solvent system for the reaction and Accordingly, one embodiment of the invention can be a process wherein the sodium aluminum hydride and the magnesium dichloride first react to produce an intermediate product comprising magnesium dialuminum hydride or chloromagnesium aluminum hydride or a mixture thereof and then extracting the amine alane from the intermediate product.

The sodium aluminum hydride which can be used with the embodiment of the invention can be that which is available from commercial sources, such as sodium aluminum hydride derived from aluminum, sodium, and hydrogen. Preferably the sodium aluminum hydride has a purity of at least about 95%, more preferably at least about 97%, most preferably at least about 99%.

The magnesium dichloride, also referred to as magnesium chloride, can be magnesium dichloride which is commercially available. However, the magnesium dichloride used can also be that which is recycled from the chloromagnesium hydride produced in reaction Scheme II. One particular method of this recycling of magnesium dichloride is that depicted in applicants' copending application U.S. Ser. No. 07/562,249, which is incorporated herein in its entirety by reference. Preferably the magnesium dichloride has a purity of at least about 95%, more preferably at least 97%.

The tertiary amine, $NR_3$, is a tertiary amine wherein R represents a carbon-containing group. The three R groups of $NR_3$ may or may not be the same. In other words, $NR_3$ represents the tertiary amines $NR'_3$, $NR'R''_2$, $NR'R''R'''$, or a mixture thereof, wherein $R',R''$ and $R'''$ are different groups from one another. One or more of $R'$, $R''$ and $R'''$40 can be an alkyl, alkene, aryl or cyclic group, saturated or unsaturated, comprising from about one to about twelve carbon atoms, preferably about one to about eight carbon atoms. For examples, one or more of $R'$, $R''$ and $R'''$ can be a $C_1$ to $C_{12}$ linear or branched alkyl such as methyl, ethyl, propyl, isopropyl, n-butyl, sec-butyl, isobutyl, 2,3-dimethylbutyl, etc. The $C_1$ to $C_{12}$ alkyls are not limited to these but can include other $C_1$ to $C_{12}$ up to heavier $C_1$ to $C_{12}$ alkyls, such as n-octyl.

Also for example, one or more R', R", R'" can be an alkene, such as 1-butene, 1-hexene or 2-hexene, or an aryl, such as phenyl or benzyl. R', R" or R'" can additionally contain one or more atoms selected from a group consisting of oxygen, sulfur, and nitrogen. Two of the R groups can be joined, such as when $NR_3$ is an N-alkylpyrrolidine.

For example, the tertiary amine, $NR_3$, can be one of the following compounds: methyldiethylamine; dimethylethylamine; dimethylbutylamine; dimethyloctylamine; N-methylpyrrolidine; trimethylamine; dimethylpropylamine; N-methyl-3-methylpyrrolidine and other similar mixed methylalkyl amines. A mixture of differing $NR_3$'s can be used. The amine conveniently can be liquid at room temperatures, but need not be.

The process for producing amine alanes can be conveniently carried out using only one solvent, preferably an aromatic hydrocarbon. Aromatic hydrocarbons which are preferred are mononuclear aromatic hydrocarbons. Among those which can be used, either singularly or in admixture, are benzene, toluene, ethylbenzene, propylbenzene, isopropylbenzene, butylbenzenes, xylenes, mesitylene, and higher alkyl (e.g. $C_5$ to about $C_8$) and dialkyl benzenes. A convenient solvent can be the commercially available mixture of benzene, toluene and xylene, commonly known as BTX. Multinuclear (i.e. multiple rings) aromatic hydrocarbons, such as 1-methylnaphthalene, 1,2,3,4-tetrahydronaphthalene, and similar compounds can be used. Mixtures of hydrocarbons predominating in aromatic components but with minor amounts of aliphatic or cycloaliphatic (i.e. alicyclic)components can also be used. The most preferred solvent is toluene.

The solvent can comprise the tertiary amine itself alone or in admixture with one or more of the above described solvents. Therefore, the solvent can consist entirely of the tertiary amine, or can be a mixture of the tertiary amine and an inert substance, or can be a mixture of the tertiary amine or one of the described solvents with or without other inert substances.

Unexpectedly, it has been discovered that solvent selection can affect stoichiometric control. That is, although Schemes I and II illustrate that the relative stoichiometric quantity of sodium aluminum hydride can control which reaction schemes is involved, there is a solvent dependency for this effect. The stoichiometric control appears valid for ether solvents, such as tetrahydrofuran (THF). However, it has been unexpectedly found that using an amine or aromatic solvent will produce chloromagnesium hydride by-product irrespective of the relative stoichmetric quantity of sodium aluminum hydride. An embodiment of the invention is a process effectively reacting sodium aluminum hydride, magnesium dichloride and a tertiary amine such that an amine alane and a magnesium compound are produced, wherein the reaction is in a solvent comprising an amine or an aromatic hydrocarbon effective to produce chloromagnesium hydride by-product.

Preferably the reaction is conducted under substantially anhydrous conditions. Trace amounts of moisture, as might normally be found in industrial solvents used for similar purposes, are acceptable.

The temperature and pressure conditions under which the reaction is conducted can be varied. Any convenient temperature which is effective can be used. The preferred temperature ranges from about 0° C. to about 100° C., more preferably from about 80° to about 100° C. A phase transfer catalyst, e.g. tris[2-(2-methoxyethoxy)ethyl] amine (i.e., TDA-1), can be used to reduce reaction temperature requirements, such as to ambient temperatures.

Any effective pressure, from as low as the vapor pressure of the reaction mixture at the temperature of the reaction to about 100 lbs per square inch, can be used, but the preferred pressure is near atmospheric pressure or that pressure which is developed in the closed reaction vessel under the reaction conditions.

As noted hereinabove, two reaction schemes are believed possible. The stoichiometric ratio of sodium aluminum hydride to magnesium dichloride ($NaAlH_4:MgCl_2$) can vary over a wide range, preferably from about 1:1 to about 2:1. More preferably the stoichiometric ratio is from 1:1 to about 1.25:1, most preferably about 1:1. Without wishing to be bound by theory, this preference may be temperature dependent, at least in part.

The reaction products from the process can be separated by using extraction processes with solvents as well as with other purification processes known to the art. The purification process used will be dependent at least in part upon the stoichiometric proportions of sodium aluminum hydride and magnesium dichloride used.

For instance, when the stoichiometric ratio of sodium aluminum hydride to magnesium dichloride approximates 1:1, a preferred purification process can be performed by the following steps:

(a) extracting the $AlH_3 \cdot NR_3$ product with toluene, (b) extracting the ClMgH with tetrahydrofuran and (c) separating the sodium chloride and any other insolubles as by-product waste.

The following examples illustrate the preferred embodiments of the invention but are not intended to limit the scope of the invention.

EXPERIMENT 1 - EXTRACTION OF AMINE ALANE FROM $NaAlH_4$ USING MAGNESIUM DICHLORIDE

The procedure for the reaction in toluene at 100° C. for 24 hours is representative. Into an approximately 25 mL Fischer-Porter reaction tube, 0.59 grams of $NaAlH_4$ (11.0 mmoles), 0.53 grams of $MgCl_2$ (5.57 mmoles), 2.0 milliliters (mL) of dimethylethylamine ($NMe_2Et$), 10.0 mL of toluene, and 0.1 mL of triethylaluminum ($Et_3Al$) were added in the dry box. The closed reaction tube was immersed in a 100° C. oil bath for 24 hours, producing a grayish solid product. The grayish solid was filtered using a fine mesh (4.5–5 micron), fritted glass, Buchner funnel. X-ray powder diffraction analysis showed ClMgH as a major component with small amounts of NaCl, $NaAlH_4$, $MgCl_2$ and Al. The filtrate evolved a total of 9.72 mmoles of $H_2$ (0.57 mmoles/gram × 17.06 grams) upon hydrolysis. The $H_2$ contained 3.2 mole percent ethane (VPC analysis of the gas collected). The net $H_2$ (9.41 mmoles) corresponds to 56% of the theoretical yield of amine alane (16.71 mmoles $H_2$) based on the amount of MgCl2 charged. Analysis of the filtrate showed a total of 3.29 mmoles Al.

EXPERIMENT 2 - EXTRACTION OF AMINE ALANE FROM NaAlH USING MAGNESIUM DICHLORIDE AND NMe₂Et

The procedure for the reaction in amine as solvent at 100° C. for 24 hours is representative. Into an approximately 25mL Fischer-Porter reaction tube, 0.54 grams of NaAlH₄ (10.0 mmoles), 0.95 g MgCl₂ (10.0 mmoles), and 11.0 mL of NMe₂Et were added and then 0.1 mL of Et₃Al was added in the dry box. The closed reaction tube was immersed in a 100° C. oil bath and the mixture stirred vigorously by a magnetic stirrer for 24 hours. The insoluble solid product was filtered using a fine mesh (4.5–5 micron) Buchner funnel. X-ray diffraction analysis revealed NaCl as the major component with a small amount of NaAlH₄. The filtrate evolved a total of 28.05 mmoles of H₂ (1.77 mmoles per g × 15.85 g filtrate) upon hydrolysis. The H₂ contained 2.0 mole percent ethane (VPC analysis of the gas collected). The net H₂ (27.5 mmoles) corresponds to 92% of the theoretical yield of amine alane (30 mmoles H₂). Analysis of the filtrate by titration showed 8.81 mmoles of soluble aluminum which corresponds to an 88% yield of amine alone.

EXPERIMENT 3 - EXTRACTION OF AMINE ALANE FROM NR₂R' USING MAGNESIUM DICHLORIDE, NMe₂Et AND TDA-1

To a 50 milliliter flask the following components were admixed: 1.11 grams (20 mmoles) of 97% sodium aluminum hydride (NaAlH₄), 1.90 grams (20 mmoles) of magnesium dichloride (MgCl₂), 15.0 grams of dry toluene, 0.65 grams (2 mmoles) of TDA-1, and 5.10 grams (70 mmoles, 2.5-fold excess) of 99% ethyldimethylamine (Me₂EtN).

This admixture was agitated overnight at room temperature under an atmosphere of nitrogen gas, producing a white slurry. The white slurry mixture was filtered through a coarse glass frit by vacuum, giving a water-white filtrate. The weight of the filtrate measured 16.35 grams. The filtrate was divided approximately evenly and analyzed. The calculated amine alane yield was 11.7 mmoles, a 58.7% yield. There was no detectable presence of hydridomagnesium chloride (HMgCl), or sodium aluminum hydride (NaAlH₄) in the analyzed solution.

EXPERIMENT 4- EXTRACTION OF AMINE ALINE FROM NaAlH₄ USING MAGNESIUM DICHLORIDE, NEt₃ AND TDA-1

Into a 50 milliliter flask the following components were admixed: 1:11 grams (20 mmoles) of 97% sodium aluminum hydride (NaAlH₄), 1.90 grams (20 mmoles) of magnesium dichloride (MgCl₂), 15.0 grams of dry toluene, 0.65 grams (2 mmoles) of TDA-1, and 7.07 grams (70 mmoles, 2.5 fold excess) of 99% triethylamine (Et₃N). The mixture was agitated overnight at room temperature under an atmosphere of nitrogen gas, producing a white slurry. Agitation was ceased and the white slurry was allowed to settle. The clear supernatant was recovered and tested by dripping 0.2 ml. of it in a few drops of methanol. Substantial activity was not detected.

The flask containing the remainder of the mixture was then fitted with a reflux condenser and nitrogen bubbler. The flask was then immersed in a 100° C. oil bath. The slurry in the flask was heated to a temperature of 80° C. to 100° C. for two hours. In about 1½ hours of the two hour period, white, fine solids of the mixture began to agglomerate. The agglomeration turned into a sticky, semi-solid mass at the bottom of the flask. This material at the bottom of the flask was not stirrable. After two hours, the flask was cooled and the liquid poured off and filtered through a 0.2 micron size filter. A water-white filtrate, 19.17 grams in weight was recovered. Analysis of the filtrate showed an amine amine yield of about 11%. The filtered solids, a hard cake, was treated with fresh toluene. The solids were then filtered and dried in a vacuum at 80° C. for two hours. Analysis of the cake by X-ray diffraction showed the major component to be sodium aluminum hydride.

What is claimed is:

1. A process comprising effectively reacting sodium aluminum hydride, magnesium dichloride and one or more tertiary amine(s) in a single solvent such that an amine alane and a magnesium compound are produced, wherein the ratio of sodium aluminum hydride to magnesium dichloride is in a range from 1:1 to 2:1.

2. The process of claim 1 wherein the sodium aluminum hydride and the magnesium dichloride first react to produce an intermediate product comprising magnesium dialuminum hydride or chloromagnesium aluminum hydride or a mixture thereof and then extracting the amine alane from said intermediate product.

3. The process of claim 1 wherein the stoichmetric ratio ranges from about 1:1 to about 1.25:1.

4. The process of claim 3 wherein the stoichmetric ratio is about 1:1.

5. The process of claim 1 wherein the tertiary amine is one or more compounds from the group consisting of tertiary amines of the formula NR₃, wherein N is nitrogen and R₃ is R'₃, R'R''₂, R'R''R''', wherein each of R', R'' and R''' independently is an alkyl, alkene or cyclic group, or wherein the tertiary amine is an alkylpyrrolidine.

6. The of claim 5 wherein NR₃ is selected from a group consisting of methyldiethylamine, dimethylethylamine, N-methylpyrrolidine, trimethylamine, dimethylpropylamine, dimethylbutylamine, dimethyloctylamine, N-methyl-3-methylpyrrolidine, and mixtures thereof.

7. The process of claim 5 wherein one or more of R', R'' and R''' comprises an alkyl, alkene or cyclic group having from about one to about eight carbon atoms.

8. The process of claim 1 wherein one or more of the tertiary amines additionally comprises one or more atoms selected from a group consisting of oxygen, sulfur and nitrogen.

9. The process of claim 1 wherein the solvent is an aromatic hydrocarbon.

10. The process of claim 9 wherein the solvent is selected from a group consisting of benzene, toluene, xylene, ethylbenzene, propylbenzene, isopropylbenzene, butylbenzene, mesitylene, 1-methylnaphthalene, 1,2,3,4-tetrahydronaphthalene and mixtures thereof.

11. The process of claim 10 wherein the solvent is toluene.

12. The process in claim 1 wherein the solvent comprises tertiary amine.

13. The process in claim 12 wherein the solvent comprises an admixture with one or more compounds selected from a group consisting of benzene, toluene, xylene, ethylbenzene, N-methylpyrrolidine, or mixtures thereof.

14. The process in claim 1 further comprising the step of extracting the amine alane with toluene and subsequently the step of extracting chloromagnesium hydride with tetrahydrofuran.

15. The process in claim 1 performed at temperatures of from about 80° C. to about 100° C.

16. The process of claim 1 wherein a phase transfer catalyst is used.

17. The process of claim 16 wherein the catalyst is tris[2-(2-methoxyethoxy)ethyl]amine.

18. The process of claim 1 wherein said reacting is in a solvent comprising an amine or an aromatic hydrocarbon effective to produce chloromagnesium hydride by-product.

* * * * *